(12) United States Patent
Lawrence et al.

(10) Patent No.: US 12,186,156 B2
(45) Date of Patent: Jan. 7, 2025

(54) PASSIVE NON-LINEAR ACOUSTIC FILTERS

(71) Applicant: TRITON SYSTEMS, INC., Chelmsford, MA (US)

(72) Inventors: Tyson Lawrence, Highlands Ranch, CO (US); Brian Fowler, Manchester, NH (US); James F. Saunders, Lowell, MA (US); Charles Dunn, Boylston, MA (US)

(73) Assignee: TRITON SYSTEMS, INC., Chelmsford, MA (US)

( * ) Notice: Subject to any disclaimer, the term of this patent is extended or adjusted under 35 U.S.C. 154(b) by 70 days.

(21) Appl. No.: 17/473,871

(22) Filed: Sep. 13, 2021

(65) Prior Publication Data
US 2022/0079813 A1 Mar. 17, 2022

Related U.S. Application Data

(60) Provisional application No. 63/077,369, filed on Sep. 11, 2020.

(51) Int. Cl.
*A61F 11/08* (2006.01)
*G10K 11/162* (2006.01)
*G10K 11/172* (2006.01)

(52) U.S. Cl.
CPC ............ *A61F 11/08* (2013.01); *G10K 11/162* (2013.01); *G10K 11/172* (2013.01); *A61F 11/085* (2022.01)

(58) Field of Classification Search
CPC ............................. A61F 11/08; A61F 11/085
USPC ....................................................... 181/135
See application file for complete search history.

(56) References Cited

U.S. PATENT DOCUMENTS

| | | | | |
|---|---|---|---|---|
| 2,850,012 | A * | 9/1958 | Becker | A61F 11/08 128/864 |
| 6,401,859 | B1 * | 6/2002 | Widmer | H04R 25/652 381/328 |
| 8,573,353 | B2 * | 11/2013 | Mulvey | A61F 11/08 181/135 |
| 2006/0042867 | A1 * | 3/2006 | Haussmann | G10K 11/172 181/135 |
| 2011/0031059 | A1 * | 2/2011 | Parish | A61F 11/08 181/129 |
| 2011/0066176 | A1 * | 3/2011 | Coole | A61B 17/56 606/198 |
| 2013/0152949 | A1 * | 6/2013 | Simon | A61F 11/08 128/868 |

(Continued)

FOREIGN PATENT DOCUMENTS

CN 105287102 A * 2/2016
CN 107517422 A * 12/2017 ............. G10K 11/04

OTHER PUBLICATIONS

International Search Report and Written Opinion for International Application No. PCT/US2021/050122 dated Dec. 15, 2021.

*Primary Examiner* — Jeremy A Luks
(74) *Attorney, Agent, or Firm* — Caldwell Intellectual Property Law

(57) ABSTRACT

Earplugs that have enhanced performance in protecting the user from high noise levels without impeding auditory awareness are described. The earplugs comprise a housing and a non-linear acoustic filter, wherein the non-linear acoustic filter can comprise a bulb. The earplugs are designed to be compatible with other types of headwear, e.g., headphones and helmets.

2 Claims, 19 Drawing Sheets

(56) References Cited

U.S. PATENT DOCUMENTS

| | | |
|---|---|---|
| 2017/0202710 A1 | 7/2017 | van 'T Hof et al. |
| 2018/0242070 A1 | 8/2018 | Slater et al. |
| 2019/0083319 A1 | 3/2019 | Harrand et al. |
| 2019/0151153 A1* | 5/2019 | Pugliano ................ B33Y 80/00 |
| 2020/0121508 A1* | 4/2020 | Chen ....................... A61F 11/10 |
| 2020/0188176 A1* | 6/2020 | Cran .................... G10K 11/162 |
| 2022/0296420 A1* | 9/2022 | Ely .................... B29C 44/1228 |

* cited by examiner

PASSIVE NON-LINEAR ACOUSTIC FILTERS

CROSS-REFERENCE TO RELATED APPLICATION

This application claims priority to U.S. Provisional Application No. 63/077,369 filed on Sep. 11, 2021, the entire contents which are incorporated herein by reference.

GOVERNMENT INTEREST

This invention was made with Government support under Contract No. M67854-17-C-6542 sponsored by the US Marine Corps. The Government has certain rights in this invention.

BACKGROUND

This disclosure relates to acoustic filters. More particularly, this disclosure relates to passive, non-linear acoustic filters. Exemplary uses of such acoustic filters is in earplugs or earmuff, although the technology behind the acoustic filter can be used in other applications.

Earplugs earmuffs that aim to maintain situational awareness, e.g., pass-through and hear-through earplugs or earmuffs, use either electronic systems or filters to attenuate only high amplitude sounds. These earplugs or earmuffs still significantly impact situational awareness because they maintain an almost closed path. Any design that includes a membrane or substantially solid structure will impair awareness. Beyond attenuation, hearing protection has generally a significant impact on the Head Related Transfer Function through the interference of the device in the pinna and the outer part of the ear canal. This results in significant localization problems such as up-down and front-back confusions.

Therefore, there is a continued need to improve earplugs or earmuffs that aim to maintain situation awareness while providing significant hearing protection against impulsive noise sources. Thus, there is a need for acoustic filters

SUMMARY

Some embodiments provide an acoustic filter comprising a housing, defining a bore; and a non-linear acoustic filter contained within the bore.

In some embodiments, the non-linear acoustic filter is selected from an end cap with two or more holes therein, one or more sets of microspheres, helical filters, mufflers, Helmholtz resonators, Tesla valves, phononic crystals, or a combination thereof.

In some embodiments, the housing is mounted within or forms a part of an earplug, an earmuff, or a helmet.

Some embodiments provide an earplug comprising a housing extending generally linearly along a longitudinal axis of the earplug and defining a bore; and a non-linear acoustic filter extending generally linearly along the longitudinal axis of the earplug and disposed at least partially in the bore, the non-linear acoustic filter having a proximal end adjacent to the eardrum, a distal end adjacent to the external orifice of the ear canal, and a middle section between the proximal end and the distal end, wherein the earplug is designed to occupy the inner part of an ear canal.

In some embodiments, the non-linear acoustic filter comprises an end cap with two or more holes therein, one or more sets of microspheres, helical filters, mufflers, Helmholtz resonators, Tesla valves, phononic crystals, or combinations thereof.

In some embodiments, the non-linear acoustic filter is an acoustic diode.

In some embodiments, the non-linear acoustic filter comprises: a first orifice coupled to the proximal end of the non-linear acoustic filter; a second orifice coupled to the distal end of the non-linear acoustic filter; and a bulb, induces diode behavior to incident sound, coupled to the middle section of the non-linear acoustic filter and acoustically connected to the first and second orifices.

Some embodiments, further comprise a first tube acoustically connected to the bulb and the first orifice.

Some embodiments, further comprise a second tube coupled to the bulb.

Some embodiments, further comprise a third tube coupled to the first orifice.

In some embodiments, the bulb is at about 0.1 mm to about 0.6 mm from the second orifice.

In some embodiments, the bulb is at about 0.2 mm to about 0.4 mm from the second orifice.

In some embodiments, the first and second orifices have a diameter of about 0.5 mm to about 3 mm.

In some embodiments, the first and second orifices have a diameter of about 0.5 mm to about 1 mm.

BRIEF DESCRIPTION OF THE FIGURES

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

In the figures.

DETAILED DESCRIPTION

Before the present devices and methods are described, it is to be understood that this invention is not limited to the particular processes, compositions, or methodologies described, as these may vary. For example, this disclosure describes various embodiments of the passive, non-linear acoustic filter employed within an earplug. The use of the described acoustic filter is not limited to earplugs, but may also be used in earmuffs, helmets, or other uses. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "a polymer" is a reference to "one or more polymers" and equivalents thereof known to those skilled in the art, and so forth.

As used herein, the term "about" means plus or minus 10% of the numerical value of the number with which it is being used. Therefore, "about 50" means in the range of 45-55.

Disclosed herein is an acoustic filter comprising a housing, defining a bore; and a non-linear acoustic filter contained within the bore. Although any suitable non-linear acoustic filter may be used, this disclosure specifically contemplates such filters which comprise an end cap with two or more holes therein, one or more sets of microspheres, helical filters, mufflers, Helmholtz resonators, Tesla valves, phononic crystals, or a combination thereof. Such filters can be useful in many applications, including but not limited to, use within, mounted within or forming a part of an earplug, an earmuff, or a helmet. For ease of disclosure, the description herein focuses on use in an earplug. The concepts discussed equally related to other uses.

Figure 1:
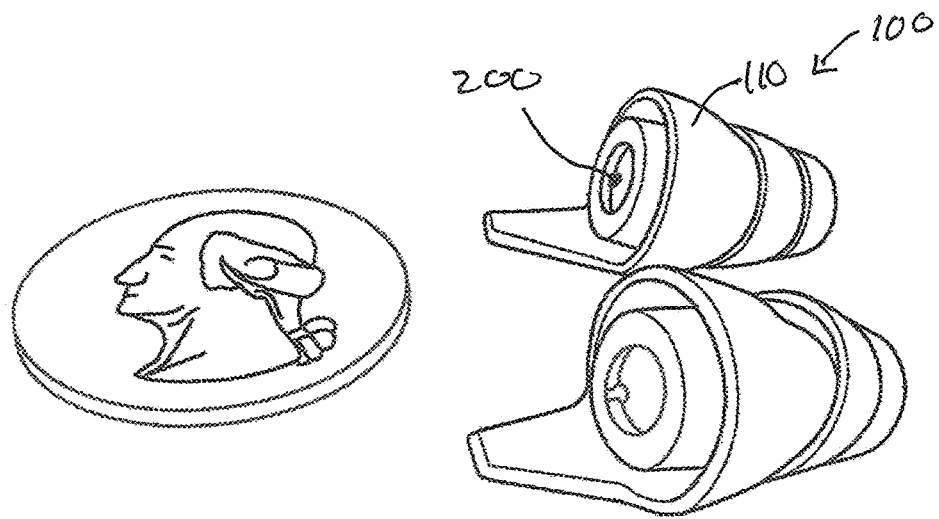
FIG. 1 is a picture showing a pair of earplugs or earmuffs each comprising a housing and a non-linear acoustic filter in accordance with aspects of the present disclosure.

In some embodiments, an earplug that protects the user from high noise levels without impeding auditory awareness is described. With reference to FIG. 1, the earplug 100 comprises a housing 110 and a filter 200. The housing 110 is designed to extend generally linearly along a longitudinal axis of the earplug 100. The filter 200 is also designed to extend generally linearly along the longitudinal axis of the earplug. The housing 110 comprises a bore and the filter 200 is disposed at least partially within the bore. In some embodiments, the filter is disposed completely within the bore.

One skilled in the art will appreciate that the housing 110 can have different sizes and shapes to accommodate the user and/or the filter. The bore of the housing can also have different sizes and shapes to accommodate the user and/or the filter. In some embodiments, the bore is composed of one or more cylindrical parts. In some embodiments, the bore is composed of one cylindrical part (as shown, for example, in FIG. 3), or two cylindrical parts, or three cylindrical parts. Some embodiments employ even more cylindrical parts.

For a bore composed of two cylindrical parts, the upper part of the housing furthest from the tympanic membrane is a first cylinder defining a first bore with an internal diameter. In some embodiments, the internal diameter is about 2.0 mm to about 7.0 mm, or about 7.0 mm, or about 6.5 mm, or about 6.0 mm, or about 5.5 mm, or about 5.0 mm, or about 4.5 mm, or about 4.0 mm, or about 3.5 mm, or about 3.0 mm, or about 2.5 mm, or about 2.25 mm, or about 2.0 mm, or any ranges that is formed from any two of those values as endpoints. The first cylinder has a depth of about 1.0 mm to about 6.0 mm, or about 6.0 mm, or about 5.5 mm, or about 5.0 mm, or about 4.5 mm, or about 4.0 mm, or about 3.5 mm, or about 3.0 mm, or about 2.5 mm, or about 2.25 mm, or about 2.0 mm, or about 1.75 mm, or about 1.5 mm, or about 1.25 mm, or about 1.0 mm, or any ranges that is formed from any two of those values as endpoints. For the bore composed of two cylindrical parts, the lower part of the housing closest from the tympanic membrane is a second cylinder defining a second bore with a diameter of about 2.0 mm to about 7.0 mm, or about 7.0 mm, or about 6.5 mm, or about 6.0 mm, or about 5.5 mm, or about 5.0 mm, or about 4.5 mm, or about 4.0 mm, or about 3.5 mm, or about 3.0 mm, or about 2.25 mm, or about 2.5 mm, or about 2.0 mm, or any ranges that is formed from any two of those values as endpoints. The second cylinder has a depth of about 8.0 mm to about 14.0 mm, or about 14.0 mm, or about 13.5 mm, or about 13.0 mm, or about 12.5 mm, or about 12.0 mm, or about 11.5 mm, or about 11.0 mm, or about 10.5 mm, or about 10.0 mm, or about 9.5 mm, or about 9.0 mm, or about 8.5 mm, or about 8.0 mm, or any ranges that is formed from any two of those values as endpoints. The first and second cylinders are mated to define a single contiguous bore.

Similarly, where multiple cylinders are employed, they are sized and configured with similar diameters and depths in the ranges described above for the first and second cylinders, to combine to from a single contiguous bore.

Any suitable non-linear acoustic filter may be used including, but not limited to filters having end caps with small holes, one or more sets of microspheres, helical filters, mufflers, Helmholtz resonators, Tesla valves, phononic crystals, or combinations thereof. Such non-linear acoustic filters are depicted in FIGS. 2-10, and described more fully below.

Figure 2:
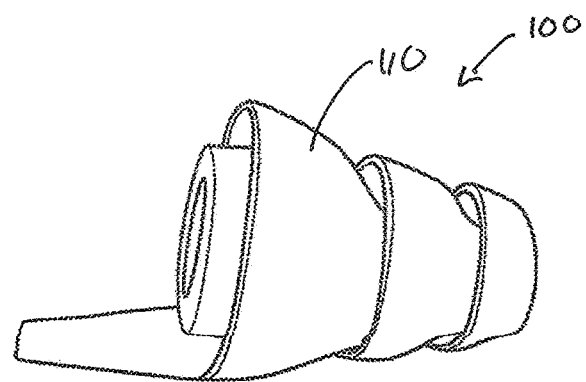
FIG. 2 is a photo showing an earplug with exemplary non-linear acoustic filters in the form of end caps with holes (2, 3, 4 and 5 hole end caps are shown outside of the earplug)
Figure 2:
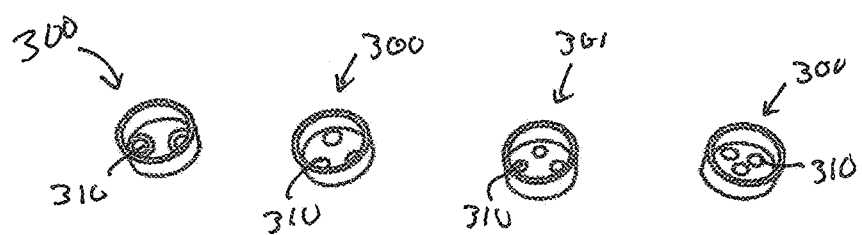

In some embodiments, the non-linear acoustic filter comprises a set of filters featuring small holes in end caps, as depicted in FIG. 2. The holes can have a diameter of about 0.3 mm, or about 0.35 mm, or about 0.4 mm, or about 0.45 mm, or about 0.5 mm, or about 0.6 mm, or about 0.7 mm, or about 0.8 mm, or about 0.9 mm, or about 1.0 mm, or any ranges that is formed from any two of those values as endpoints. The caps can have a diameter of about 2 mm, or about 2.5 mm, or about 3 mm, or about 3.5 mm, or about 4 mm, or any ranges that is formed from any two of those values as endpoints, and the caps can fit snugly into a bore, such as the lower bore, of the housing. FIG. 2 depicts an ear plug 100 and four different end caps 300. The end caps 300 as shown from left to right include 2, three, 4 and 5 holes 310, respectively.

Figure 3:
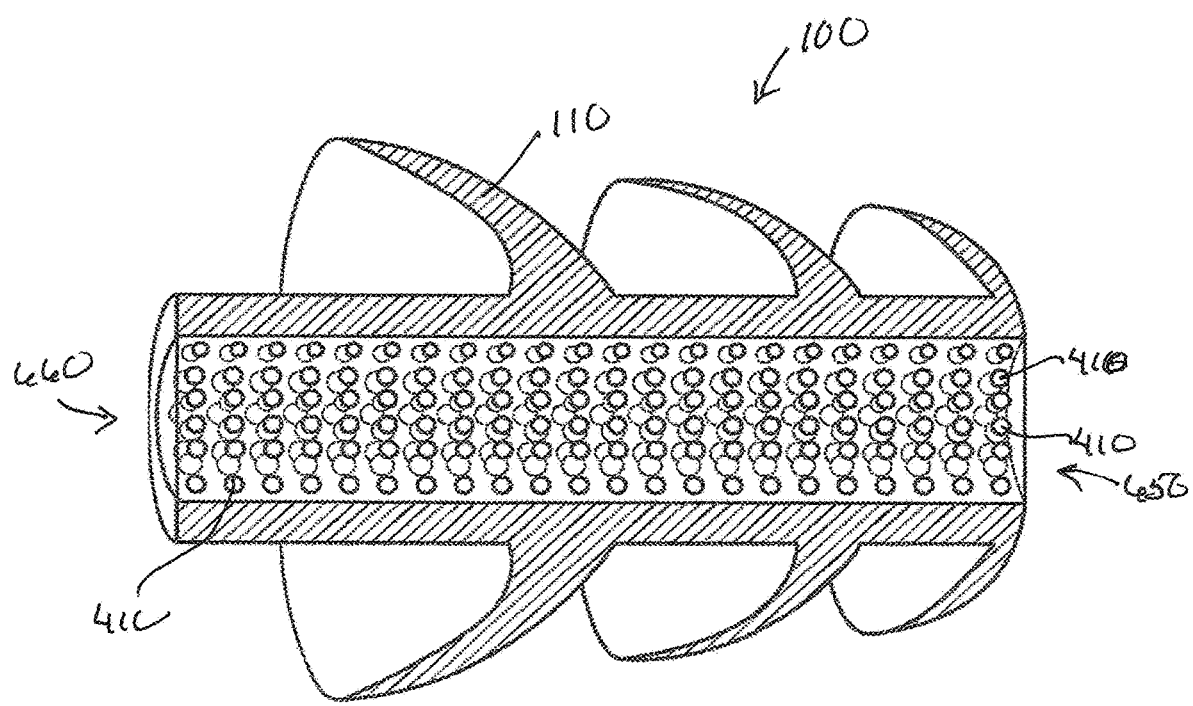
FIG. 3 depicts a cross-sectional view of an earplug where the exemplary non-linear acoustic filter in the form of a plurality of microspheres.

In some embodiments, the filter comprises one or more sets of solid microspheres 410 (e.g., polyethylene microspheres). The microspheres 410 may be any suitable material including, but not limited to polymers, plastics, resins, glass, metal, etc. In some embodiments, the microspheres have a diameter of about 345 microns, or about 355 microns, or about 365 microns, or about 375 microns, or about 385 microns, or about 395 microns, or about 405 microns, or about 415 microns, or about 425 microns, or about 435 microns, or any ranges that is formed from any two of those values as endpoints. In some instances, the filter may include a mix of microspheres of different sizes and/or materials. The microspheres are sealed into the plastic caps with a polyester mesh (e.g., McMaster-Carr part #93185T4). The microspheres can be sealed into plastic caps with a polyester mesh, for example, with openings of 0.14 mm and 24% open area (McMaster-Carr part #93185T4). FIG. 3 depicts such an arrangement. A plurality of microspheres are placed with the bore along the linear axis of the housing.

Figure 4:
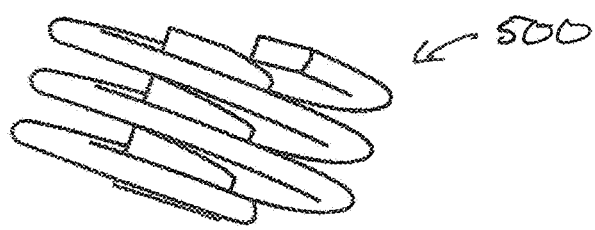
FIG. 4 depicts a view of filter in a form of a negative helix.

Other types of filters can be used with the housing. For instance, the filter can have several helical based filters such as filters with a "negative helix." A "negative helix" refers to the situation where the void forms a helical structure. One will appreciate that to achieve this, the solid portion need not also have a helical shape. Other helical designs can also be employed. FIG. 4 is representative of a negative helical design 500. The angle of the helix may be varied, the distance between platform may be uniform or varied. The platform surface may be flat, bumpy, corrugated or other shape. Any suitable length or diameter maybe employed depending up the housing within which the negative helix is placed. The voids between platform may be hollow or filled, for example with microspheres described above.

Figure 5:
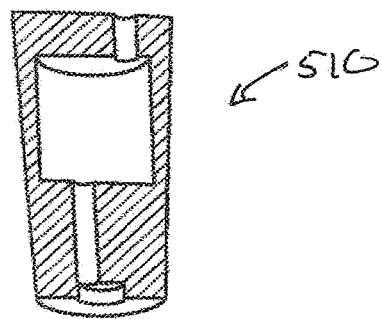
FIG. 5 depicts a muffler design for use as a non-linear acoustic filter in accordance with some embodiments.

The filter can have a muffler based design, wherein the design features an inlet and outlet aperture with a small reverberation chamber to attenuate impulsive noise. These mufflers can be made by any suitable means, including but not limited to 3D printing. FIG. 5 is representative of a muffler design 510. The filter can have a diameter substantially similar to the bore as described above, such that the filter substantially fills the bore.

Figure 6:
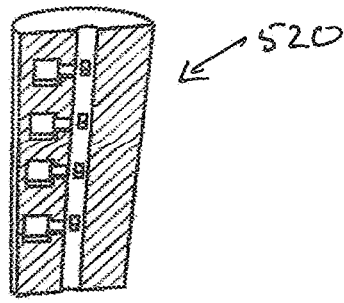
FIG. 6 shows an example of Helmholtz resonators for use as a non-linear acoustic filter in accordance with some embodiments.

The filter can have a narrow aperture with branching Helmholtz resonators. This design allows for a wider aperture through the filter because the Helmholtz resonators can absorb some of the impulsive noise. The filter can have a diameter substantially similar to the bore as described above, such that the filter substantially fills the bore A representative Helmholtz resonator 520 suitable for fitting within the bore of a housing is shown in FIG. 6.

Figure 7:
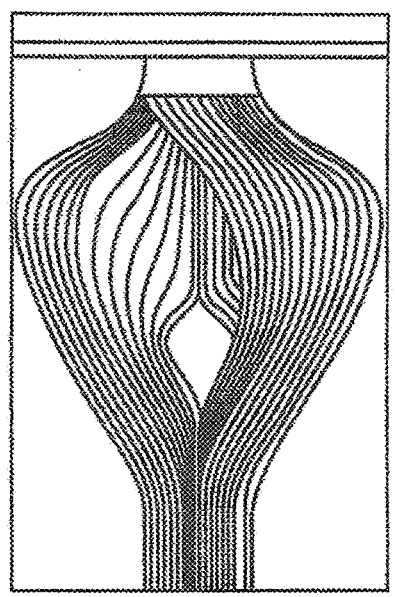
FIG. 7 depicts Tesla valve for use as a non-linear acoustic filter in accordance with some embodiments.

The filter can be a non-linear acoustic filter such as a non-linear acoustic filter with a fluid diode design modeled after a Tesla Valve, such as depicted in FIG. 7. This valve is designed to introduce significant flow turbulence in one direction, while offering little resistance in the other direction. Positioning this filter in the restricting direction can offer a non-linear effect as "flow" (amplitude) increases. The filter can also have one of a variety of cross-sectional areas, that can vary through the length of the filter, where the shapes and effective cross-sectional areas have finely tuned hydraulic diameters 630 to create the desired attenuation.

Other filters may also employ controlled hydraulic diameter 630 along the length of the bore through the filter can be tuned and arranged to create a non-linear filter.

Figure 8:
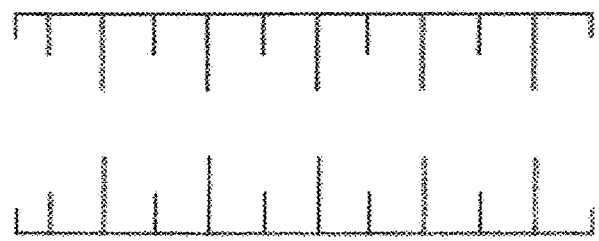
FIG. 8 shows an exemplary non-linear acoustic filters in accordance with some embodiments.

Other types of filters may be used as well. Several are discussed below:

An "acoustic interference" design includes a breadboard with layered chambers of different diameters, creating a ridged effect inside the breadboard while still maintaining an open path. A simplified schematic of an acoustic interference design is depicted in FIG. 8.

Figure 9:
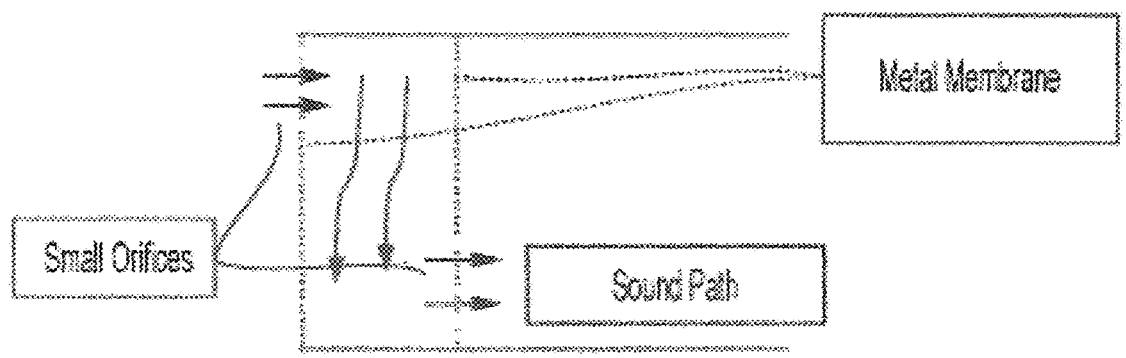
FIG. 9 shows an exemplary non-linear acoustic filters in accordance with some embodiments.
Figure 10:
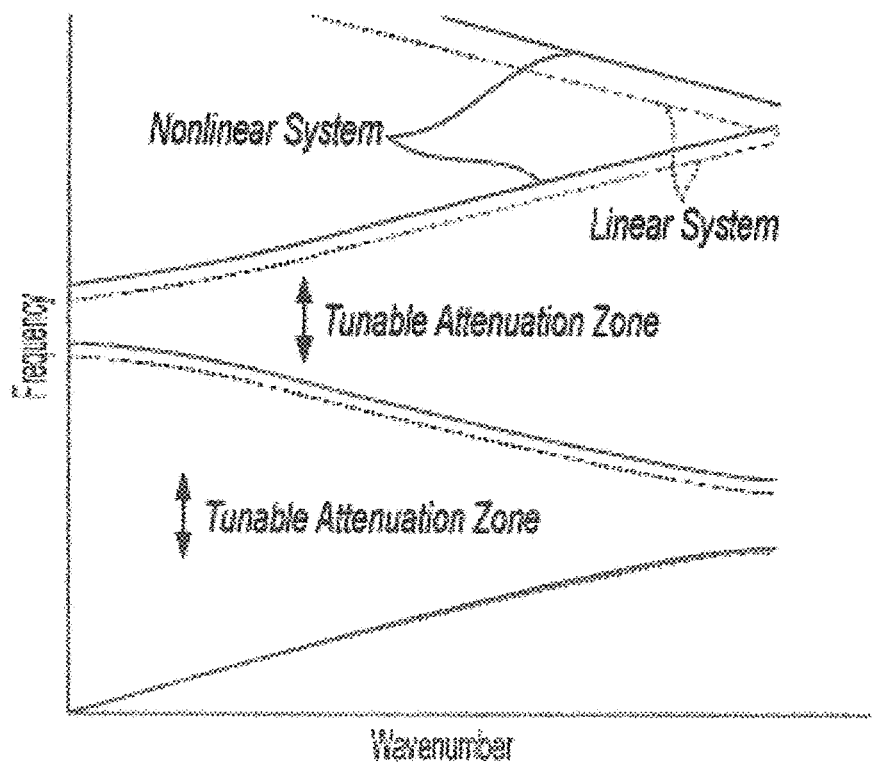
FIG. 10 depicts "band gaps" that block sound at certain frequencies in metamaterial structures and phononic crystals in accordance with some embodiments.

In addition to single membranes, a more complex layered concept was designed to incorporate a torturous sound path and viscous damping effect with the impulse noise damping of a perforated membrane (see FIG. 9). This design uses two metal (e.g. aluminum) membranes spaced a short distance apart. Small orifices made on opposite sides of the two membranes ensure there is no straight path for the sound to travel. Similar to the design of a muffler, this concept aims to trap high intensity loud sounds in the center chamber while allowing softer sounds through. Other materials such as plastics, polymers, glass, or combinations thereof could also be used. Single or multiple perforated plates (more than two) can be used. Also, the perforations can be uniform or have non-uniform hole sizes and/or non-uniform hole patterns. Perforation diameter is between 0.25 mm to 1 mm.

In some embodiments, the filter comprises of phononic crystals. Acoustic metamaterials and phononic crystals are designed structures that can be tuned for response at specific frequencies and for acoustic refraction. One unique feature of metamaterials is the possibility for negative refractive index. Metamaterial structures and phononic crystals can also be designed to have "band gaps" that block sound at certain frequencies (see for example, FIG. 10).

These band gaps can be made to shift with changes in wave amplitude, shown on the frequency graph as a shift from the gray to black lines. This non-linear behavior can be harnessed to affect attenuation within the range of human hearing.

Finally, the idea of using beads in the particle filter that have a complex resonating structure was also indicated, this could be combined with the particle filters as an option for the particles.

Figure 11:
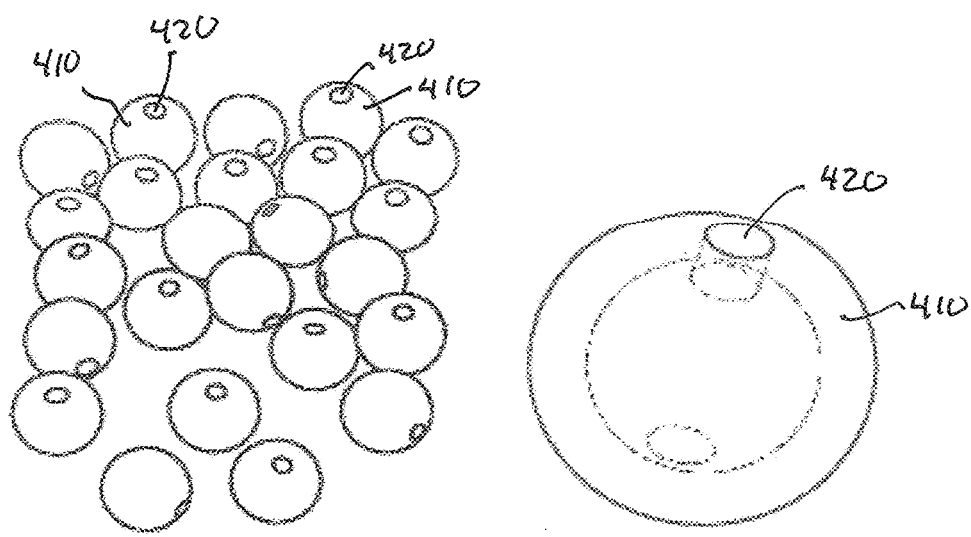
FIG. 11 shows hollow beads that act as a local Helmholtz Resonator.

Each particle within the system will act as a local Helmholtz Resonator, by using hollow beads (see FIG. 11) that are open on one side. Small hollow beads are commercially available, and can be easily manufactured into Helmholtz Resonators using vibration for orientation and a film adhesive to cover up one side of the bore.

Similarly, superabsorber pads, such as low frequency "super absorber" pads, can be spaced in the earplug for low frequency noise attenuation.

Combinations of these filter types may also be used. See FIG. 12. Some embodiments are designed to be modular, particularly those with 2 or more cylinders, so that each cylinder could contain a different filter or combination of filters.

The non-linear acoustic filter disclosed herein has a proximal end adjacent to the eardrum, a distal end adjacent to the external orifice of the ear canal, and a middle section between the proximal end and the distal end. The non-linear acoustic filter can have a first orifice 660 coupled to the proximal end of the non-linear acoustic filter and a second orifice 650 coupled to the distal end of the non-linear acoustic filter 600. The earplug can further comprise a bulb coupled to the middle section of the non-linear acoustic filter and fluidly connected to the first and second orifices. The earplug can further comprise a first tube fluidly connected to the first orifice, a second tube connected to the bulb, and a third tube coupled to the first orifice. In some embodiment, the second and third tubes are fluidly connected. In some embodiments, the second and third tube are not fluidly connected.

In some embodiments, the distance 630 between the filter's center feature 610 and the external wall of the filter is about 0.05 mm, or about 0.1 mm, or about 0.2 mm, or about 0.3 mm, or about 0.4 mm, or about 0.5 mm, or about 0.6 mm, or about 0.7 mm, or about 0.8 mm, or about 0.9 mm, or about 1.0 mm, or any ranges that is formed from any two of those values as endpoints. In some embodiments, the diameter of the first orifice is about 0.50 mm, or about 0.55 mm, or about 0.60 mm, or about 0.65 mm, or about 0.70 mm, or about 0.75 mm, or about 0.80 mm, or about 0.85 mm, or about 0.9 mm, or about 0.95 mm, or about 1.00 mm, or about 1.05 mm, or about 1.10 mm, or about 1.15 mm, or about 1.20 mm, or about 1.25 mm, or about 1.30 mm, or about 1.35 mm, or about 1.40 mm, or about 1.45 mm, or about 1.50 mm, or about 1.55 mm, or about 1.66 mm, or about 1.65 mm, or about 1.70 mm, or about 1.75 mm, or about 1.80 mm, or about 1.85 mm, or about 1.90 mm, or about 1.95 mm, or about 2.00 mm, or any ranges that is formed from any two of those values as endpoints. In some embodiments, the diameter of the second orifice is about 0.50 mm, or about 0.55 mm, or about 0.60 mm, or about 0.65 mm, or about 0.70 mm, or about 0.75 mm, or about 0.80 mm, or about 0.85 mm, or about 0.9 mm, or about 0.95 mm, or about 1.00 mm, or about 1.05 mm, or about 1.10 mm, or about 1.15 mm, or about 1.20 mm, or about 1.25 mm, or about 1.30 mm, or about 1.35 mm, or about 1.40 mm, or about 1.45 mm, or about 1.50 mm, or about 1.55 mm, or about 1.66 mm, or about 1.65 mm, or about 1.70 mm, or about 1.75 mm, or about 1.80 mm, or about 1.85 mm, or about 1.90 mm, or about 1.95 mm, or about 2.00 mm, or any ranges that is formed from any two of those values as endpoints.

The earplugs or earmuffs disclosed herein can be used in many applications. For instance, some of the earplugs or earmuffs disclosed herein can be used by soldiers. Situational awareness in a combat mission is crucial for military safety and cannot be compromised. To maintain the ability to hear and localize soft noises in the field, personnel often forgo hearing protection, leading to later hearing related injury. The earplugs or earmuffs disclosed herein maintain nearly true hearing in the absence of loud noises and automatically engages to attenuate louder sounds such as gunfire.

EXAMPLE

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Earplugs with Non-Linear Acoustic Filter

Figure 13:
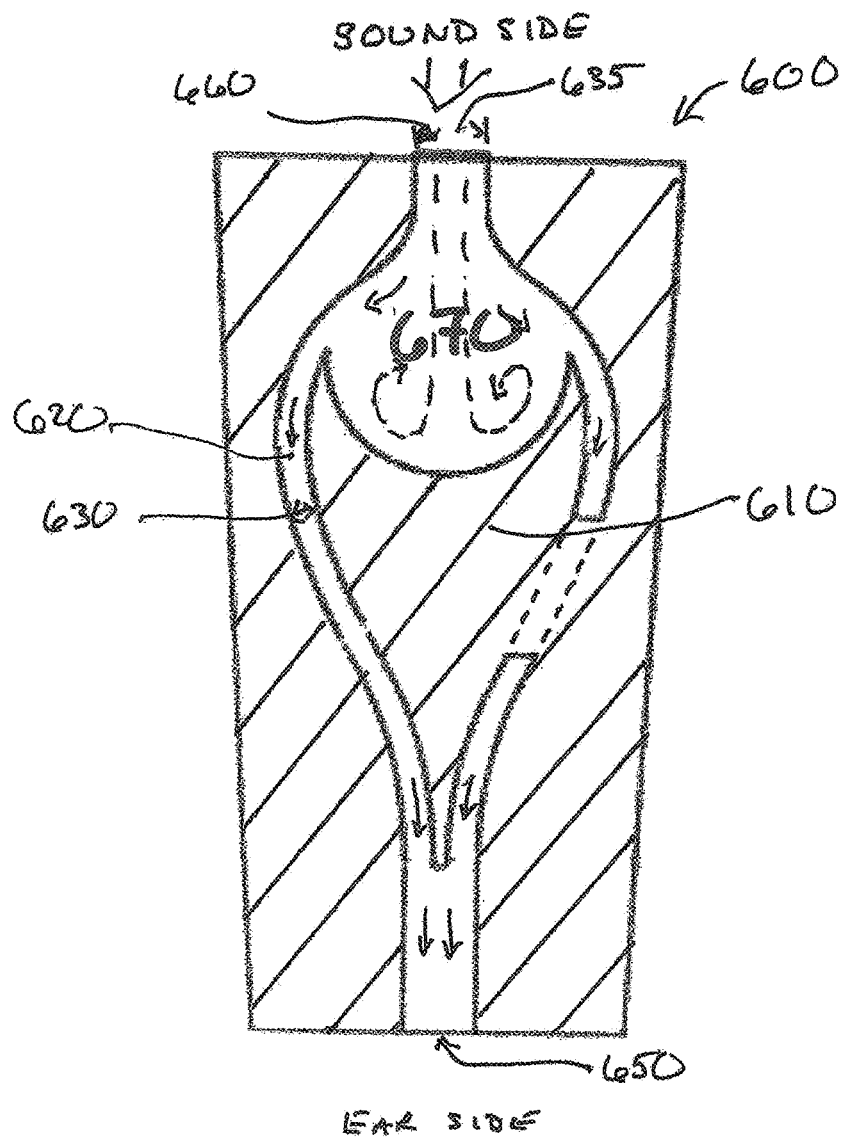
FIG. 13 is a schematic representation of a cross section of a non-linear acoustic filter in accordance with aspects of the present disclosure.

Earplugs with non-linear acoustic filter are fabricated (FIG. 1A). Silicone flanged Westone Tru Universal Replacement Eartips are used as housing. A non-linear acoustic filter (FIG. 13) in the form of a Tesla valve is inserted into the bore of the housing. The non-linear acoustic filter is printed using a RenShape SL 7820 high resolution stereolithography build in 0.0508 mm (0.200 inch) layers. The material used in the process is Accura® 25 plastic which simulates the properties and aesthetics of polypropylene and has characteristics necessary for this part.

Example 2

Performance of Earplugs with Non-Linear Acoustic Filter

The earplug exhibits the performance characteristics summarized in Table 1.

TABLE 1

| Performance Characteristic | Test Condition | Result |
| --- | --- | --- |
| Situational Awareness | Detection Threshold | <5 dB increase from Open Ear |
| | Recognition/Identification | Not statistically distinct from Open Ear |
| | Localization | Not statistically distinct from Open Ear |
| | Communication | Not statistically distinct from Open Ear |

TABLE 1-continued

| Performance Characteristic | Test Condition | Result |
| --- | --- | --- |
| Impulsive Noise Protection | Shock Tube (150 dB) | 17.1 ± 2.6 IPIL (Impulse Peak Insertion Loss) |
| | Shock Tube (168 dB) | 24.9 ± 2.2 IPIL |
| | AR-15 Firearm (158 dB) | 20.4 IPIL |
| | 9 mm round (153 dB) | 22.8 IPIL |
| | ISL Test (195 dB) | 31 ± 0 IPIL (quick look data) |
| Continuous Noise Protection | Test mannequin (105 dB) | Meaningful hearing protection |
| | NRR Rating | 12 or less confirmed |

Example 3

Performance Comparisons of Earplugs with Non-Linear Acoustic Filter

Figure 14:
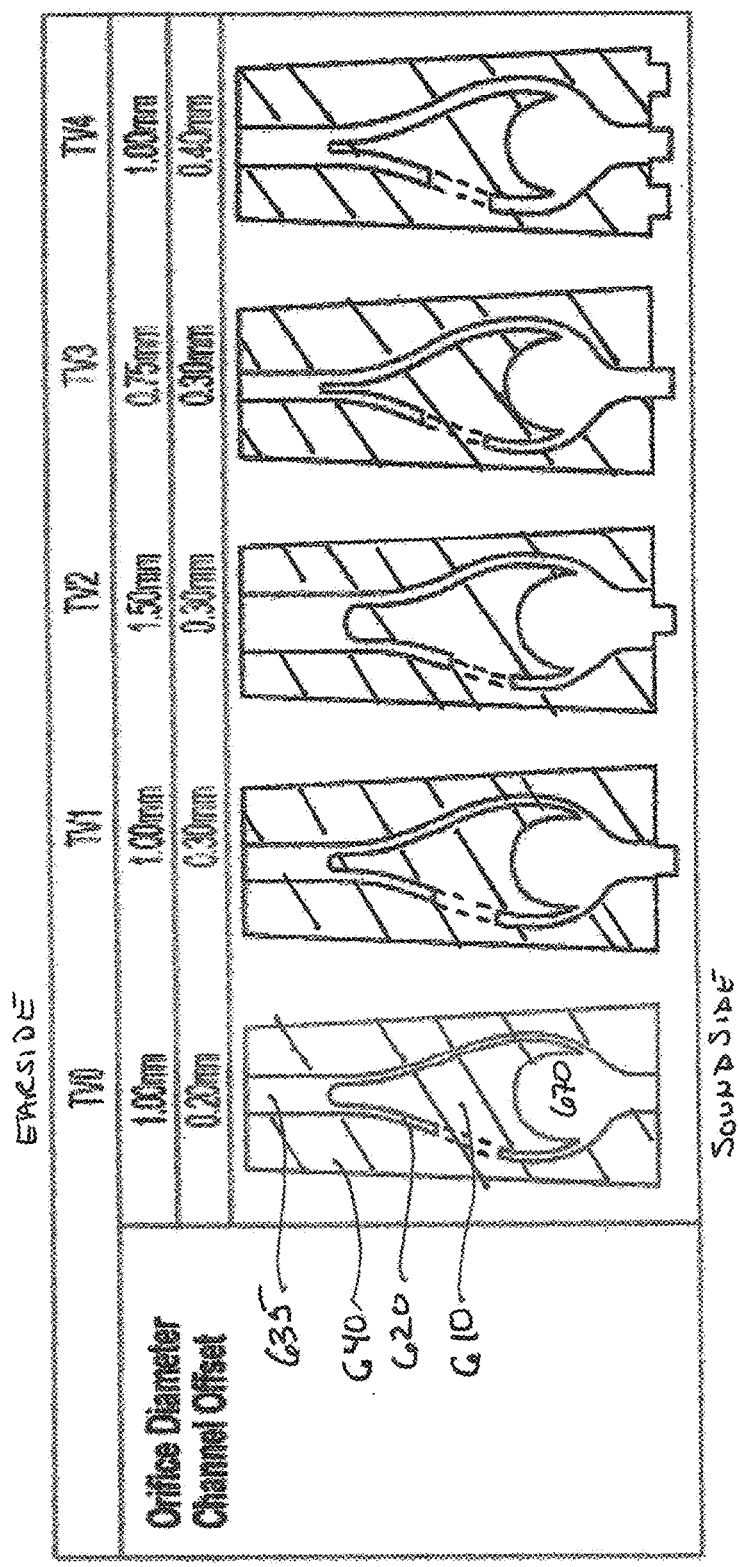
FIG. 14 is a schematic representation of cross section adjustment to control the performance of non-linear acoustic filters in accordance with aspects of the present disclosure.
Figure 15:
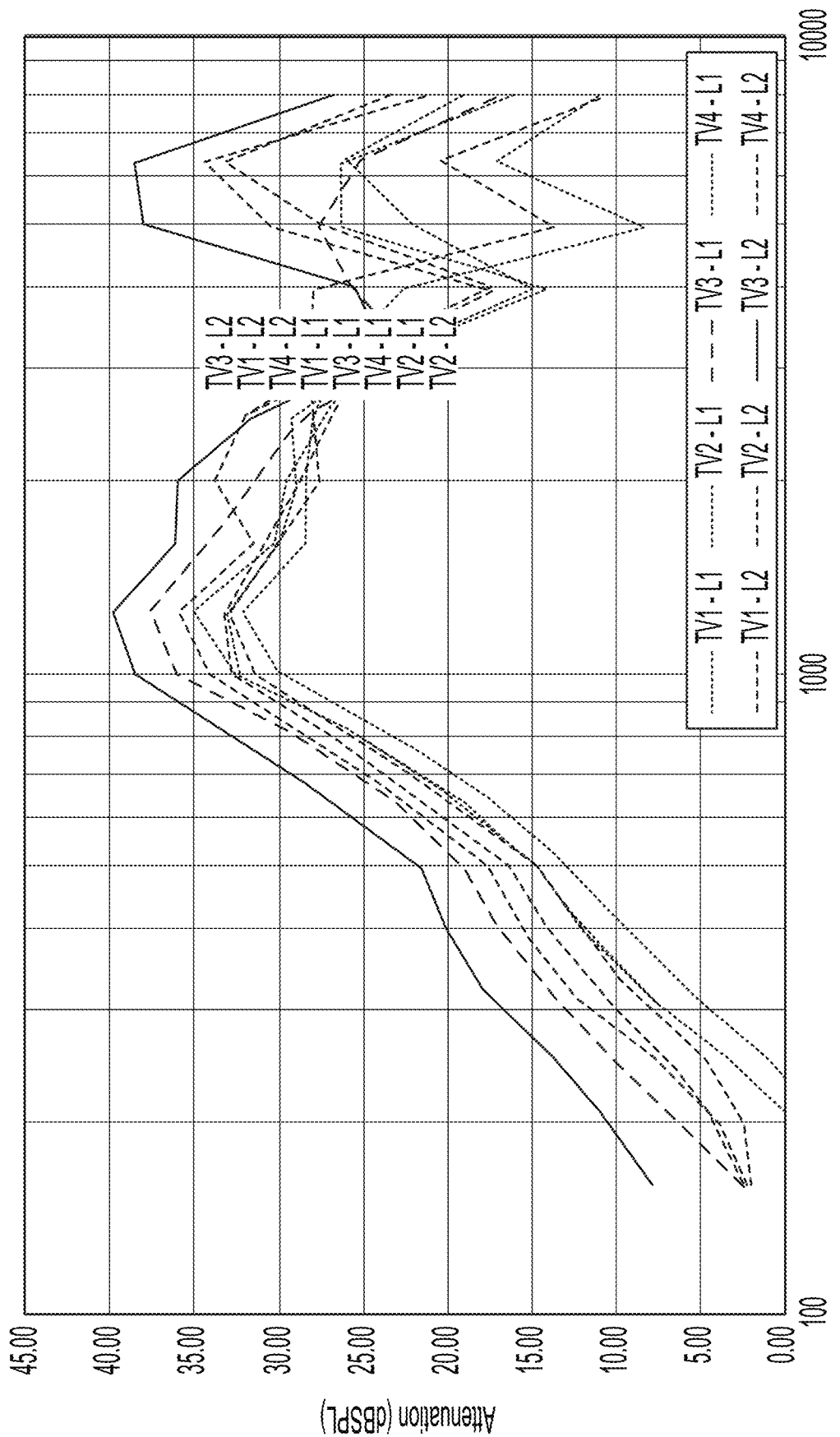
FIG. 15 is a graph showing the ISIL performance of non-linear acoustic filters at 150 dB (L1) and 158 dB (L2) in accordance with aspects of the present disclosure.
Figure 16:
FIG. 16 is a graph showing the IPIL performance of non-linear acoustic filters at 150 dB (L1) and 158 dB (L2) in accordance with aspects of the present disclosure.

Earplugs with non-linear acoustic filter (here a Tesla valve) of different dimensions are fabricated (FIG. 14) and compared (FIGS. 15 and 16). The non-linear acoustic filters have an orifice diameter (i.e., aperture at both the source side and ear-side of the filter) of 1.00 mm (filters TV0, TV1, and TV4), 1.50 mm (filter TV2), and 0.75 mm (filter TV 3). The non-linear acoustic filters have a channel offset (i.e., distance between the filter "bulb" and the surrounding material) of 0.20 mm (filter TV0), 0.30 mm (filters TV1, TV2, and TV3), and 0.40 mm (filter TV4). FIG. 15 shows the results of ISIL (Impulse Spectral Insertion Loss) shock tube tests on the non-linear acoustic filter at two impulse levels. FIG. 16 shows the IPIL results of shock tube tests on the non-linear acoustic filter at two impulse levels.

Example 4

Modeling

The Pressure Acoustics module for COMSOL Multiphysics simulations is used to simulate and compare the results of applying high amplitude shock waves to non-linear acoustic filters.

Modeling of Simple Channel

Figure 17:
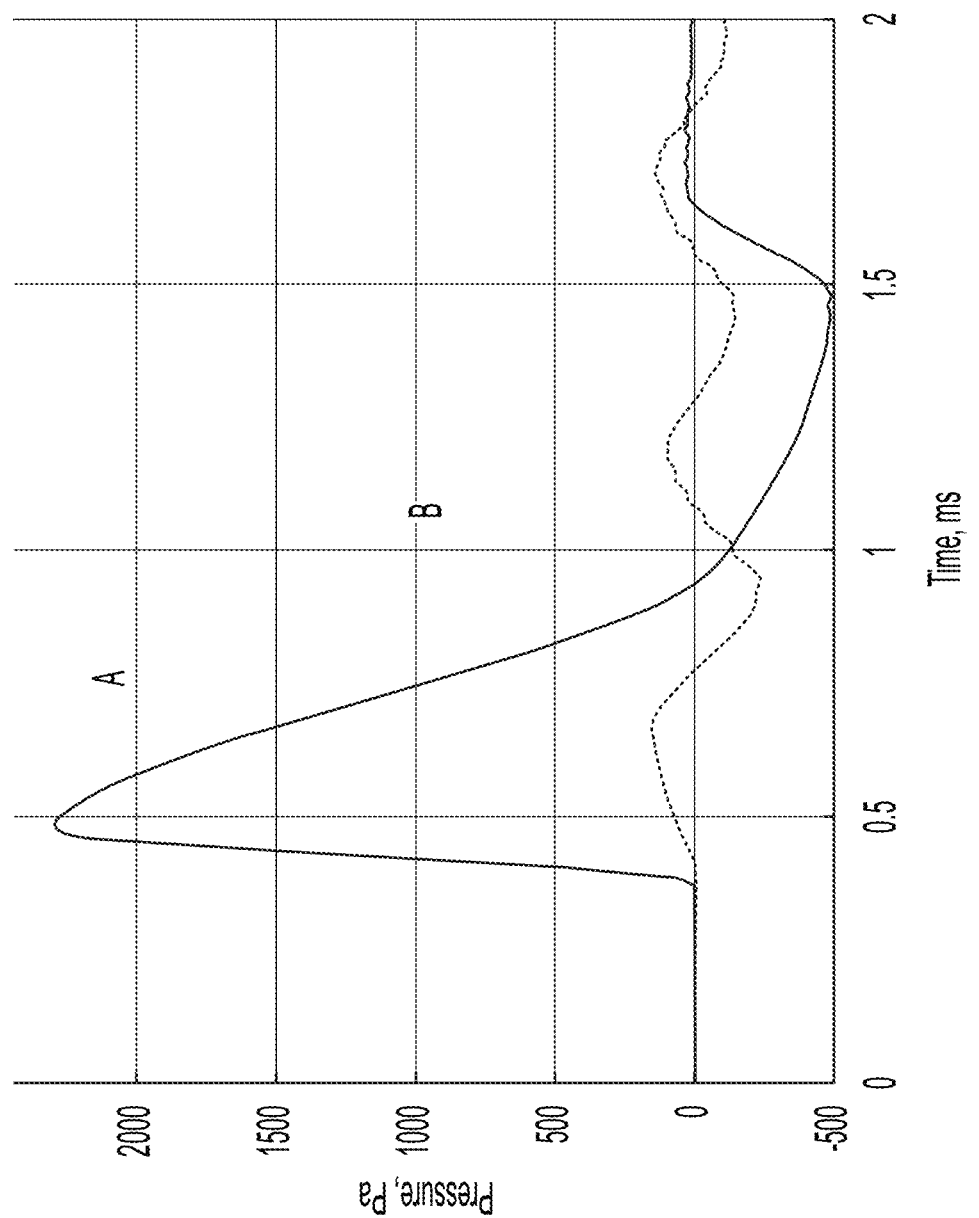
FIG. 17 is a graph showing the simulated blast response where A is incident on the filter and B is the filtered output. This simulation used a channel with 10 mm length and 0.3 mm diameter in accordance with aspects of the present disclosure.
Figure 18:
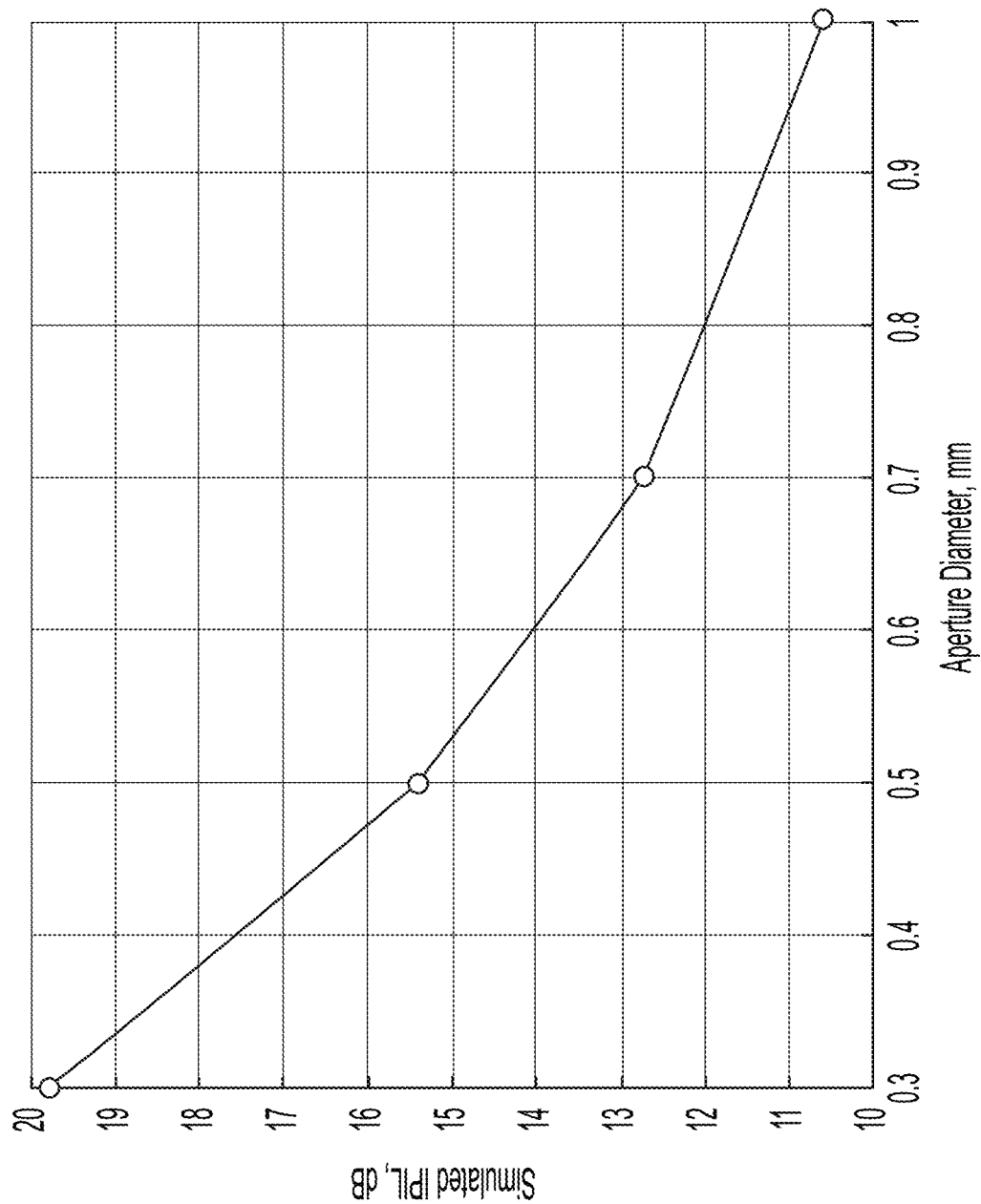
FIG. 18 is a graph showing the simulated IPIL of a channel with 10 mm length and 0.3 mm to 1.0 mm diameters in accordance with aspects of the present disclosure.

The IPIL for a set of simple channels with a length of 10 mm and diameters of 0.3, 0.5, 0.7, and 1.0 mm are performed. The incident shock wave used in the simulation has a peak pressure of 160 dBSPL and a duration (i.e., time from the beginning of the impulse noise until the first zero crossing after the drop from peak pressure) of 0.5 ms. FIG. 17 shows the simulated pressure levels immediately prior to the non-linear acoustic filter (A curve) and just after the non-linear acoustic filter (B curve) for a channel with 0.3 mm diameter, a straight bore, and IPIL of 19.7 dB. FIG. 18 shows the attenuation for channel diameters from 0.3-1.0 mm.

Modeling of Non-linear Acoustic Filter

Figure 19:
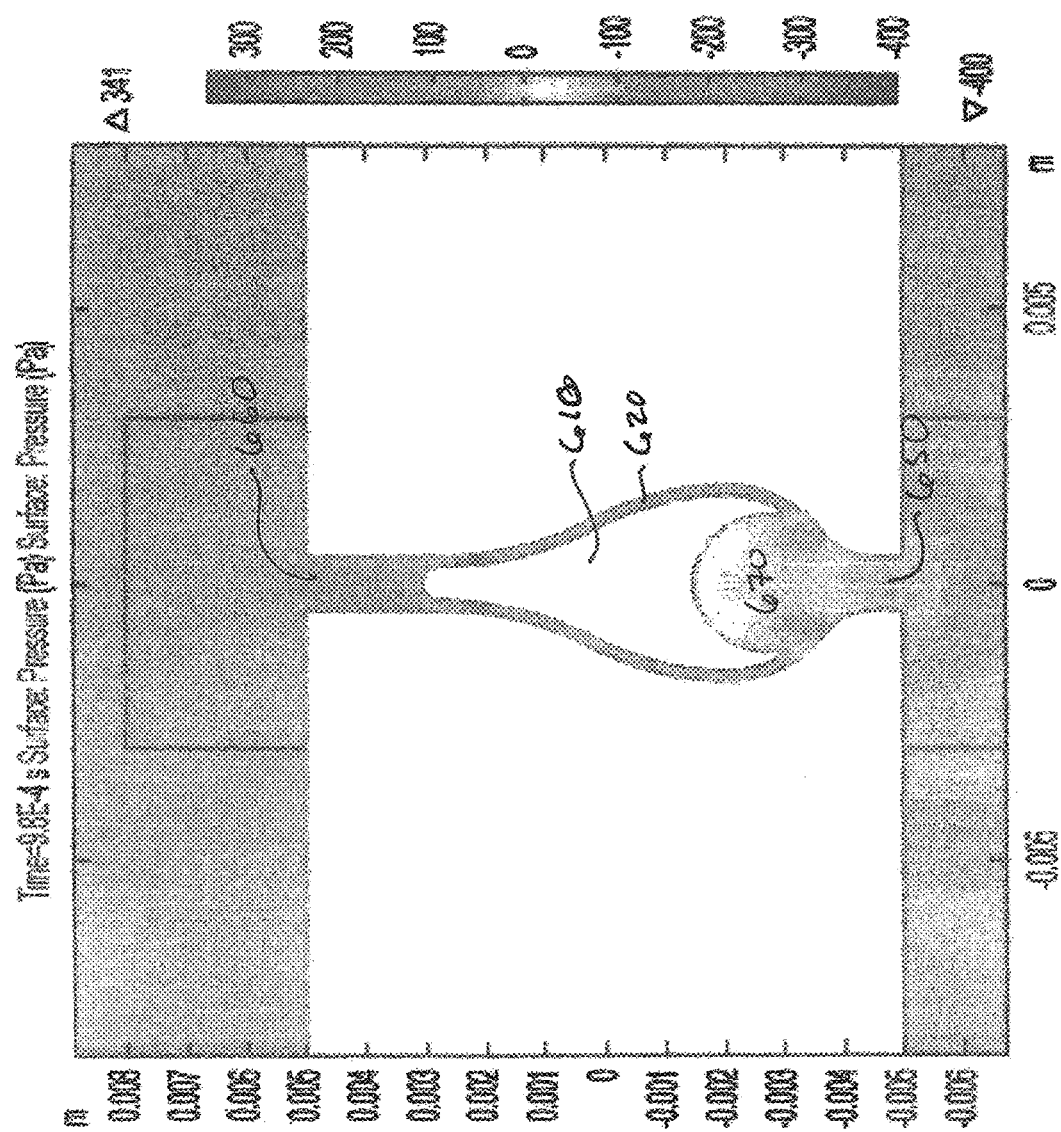
FIG. 19 is a diagram showing the simulated acoustic pressure in a non-linear acoustic filter in accordance with aspects of the present disclosure.
Figure 20:
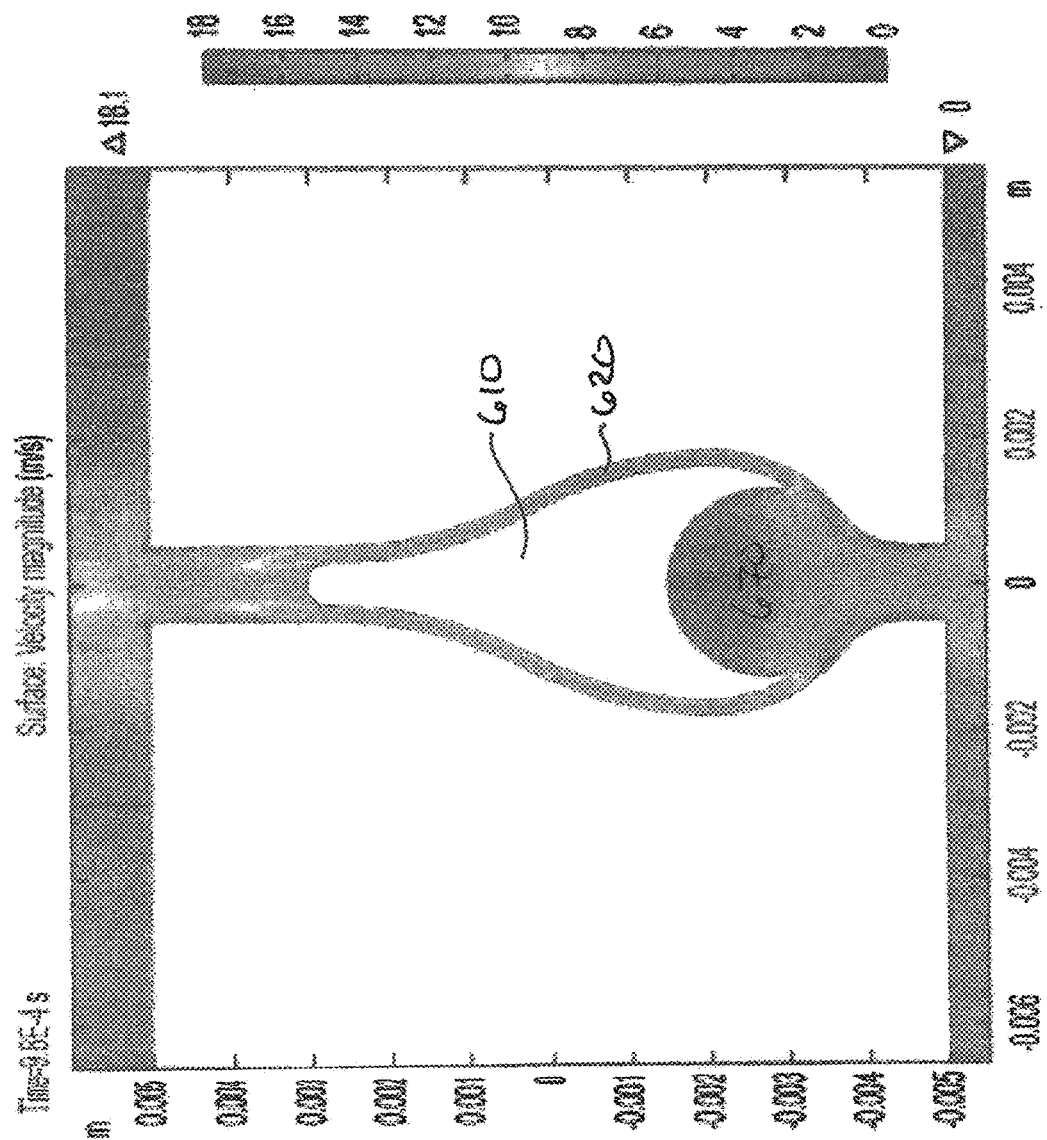
FIG. 20 is a diagram showing the fluid velocity through a simulated non-linear acoustic filter in accordance with aspects of the present disclosure.
Figure 21:
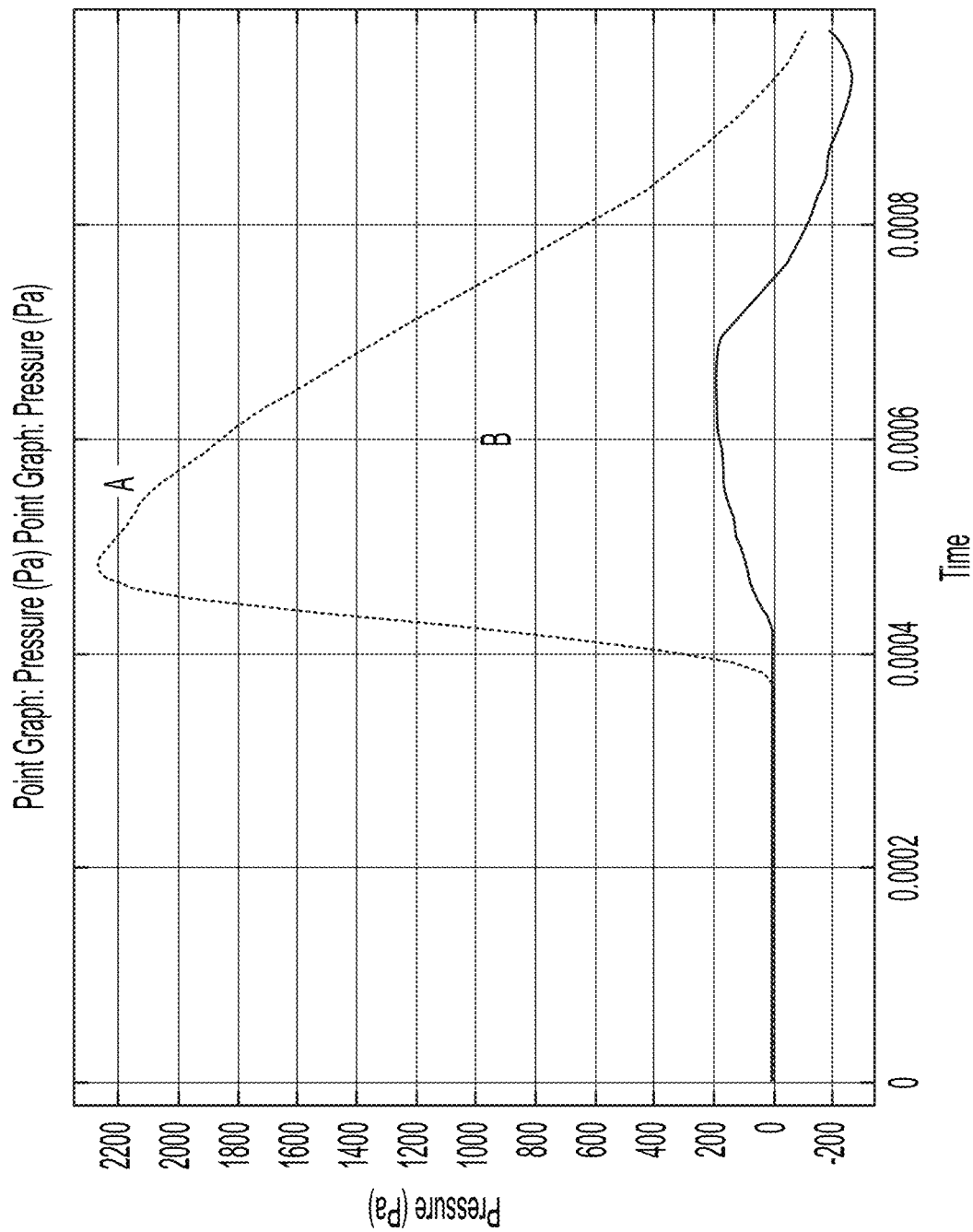
FIG. 21 is a graph showing the simulated filter response for the non-linear acoustic filter TV3 subjected to a 160 dB SPL impulse where A is the pressure just prior to the filter and B is the pressure just after the filter in accordance with aspects of the present disclosure.

The shock wave interacting with the non-linear acoustic filters is modeled. FIGS. 19 and 20 show plots of the acoustic pressure (FIG. 19) and the fluid velocity (FIG. 20) in the filter as the shock wave begins to interact with the filter. In these plots, the shock wave is propagating from the bottom of the figure towards the top. FIG. 21 shows the non-linear acoustic filter TV3 simulated to have an IPIL of 20.4 dB when subjected to a 160 dB SPL blast that is consistent with the measurement from the shock tube testing. In this plot, the simulated pressure is showed just prior to the non-linear acoustic filter (A curve) and just after the non-linear acoustic filter (B curve).

Axisymmetric Modeling of Non-Linear Acoustic Filter

Figure 22:
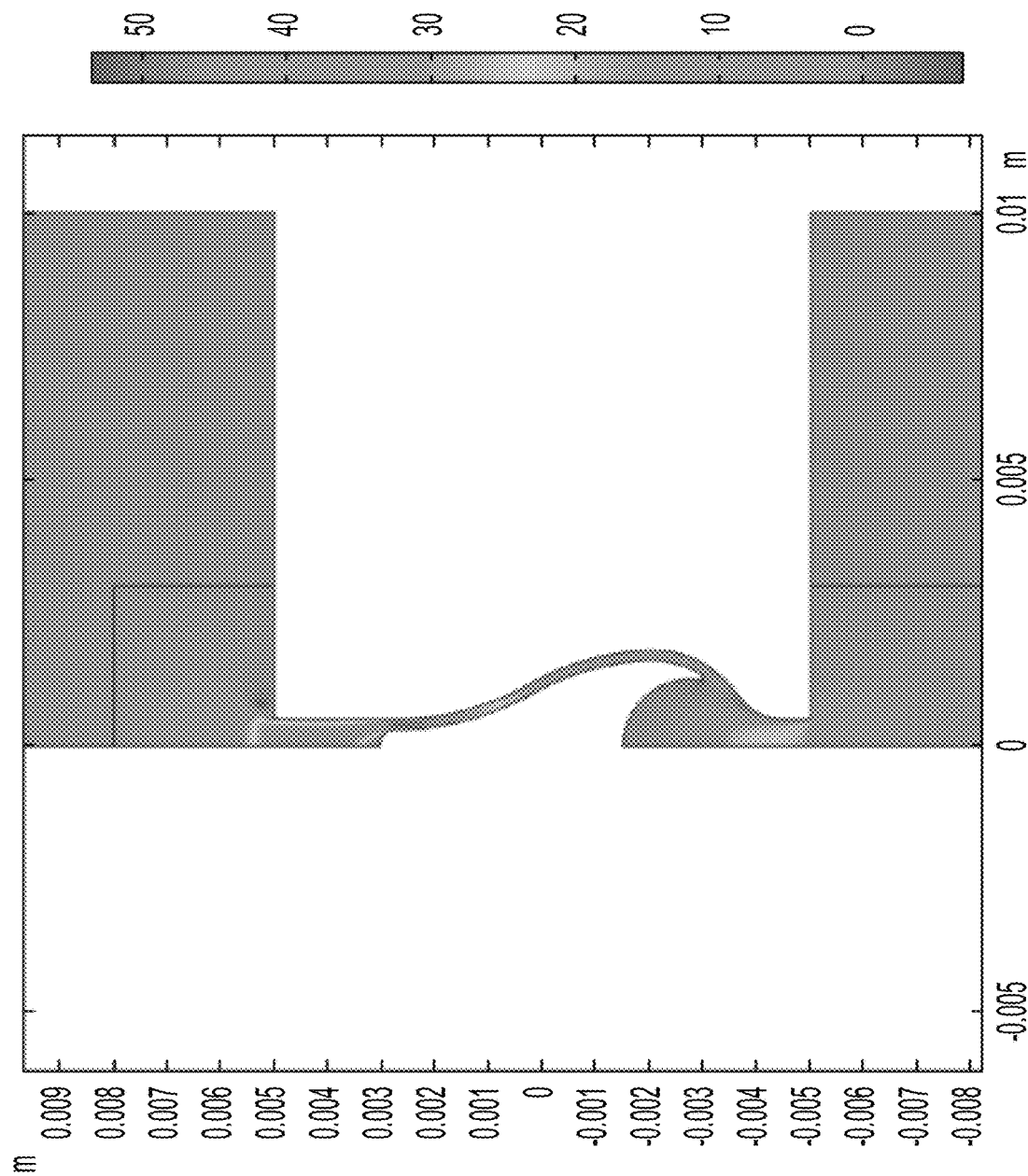
FIG. 22 is a diagram showing the simulated axisymmetric fluid particle velocity of shockwave encountering a non-linear acoustic filter where the fluid speed increases as it moves down the channel in accordance with aspects of the present disclosure.

The axisymmetric modeling of non-linear acoustic filter is performed. The axisymmetric modeling allows to decrease the mesh size and capture the acceleration of the fluid-particle velocity as it encounters the non-linear acoustic filter. A plot of the fluid particle velocity when a 170 dB shockwave encounters the non-linear acoustic filter is shown in FIG. 22. As the fluid moves up the channel toward the exit, the radius is decreasing. This causes the fluid to further accelerate which creates turbulent flow at the exit of the filter. Transitioning form laminar to turbulent flow in the aperture increases the dissipation of the acoustic energy.

Example 5

Continuous Noise Testing of Non-Linear Acoustic Filter

SoundCheck test sequences according to ANSI S12.42-2010 for Acoustic Test Fixture (ATF) testing are performed.

Test Stimuli

The test stimulus has the follow characteristics:
Broadband random noise in each OTO (One Third Octave) band centered from 100 Hz to 10,000 Hz;
Rolls off >3 dB at 80 Hz and 12,500 Hz;
Rolls off >12 dB/octave below 80 Hz and above 12,500 Hz;
Min/max difference between OTO band levels<10 dB;
Difference between adjacent OTO band levels<3 dB (except when overall SPL exceeds 115 dB, in which case the variation shall be reported);
Overall SPL for single level testing: 105 dB±3 dB;
Overall SPL for level-dependent testing according to Section 9.5.7 per the standard: 75, 85, 95, and 105 dB, each level 3 dB;
SPL in each OTO band centered from 100 Hz to 10,000 Hz>85 dB (20 dB below the overall SPL target);
For passive HPDs, the above levels can be adjusted to 70 dB and 90 dB respectively; and
OTO band SPLs at the reference point shall be reproducible to within ±0.5 dB Per the standard, this stimulus is validated every morning prior to testing and every evening following testing.

Test Protocol

Triton has Developed

A test sequence for continuous noise testing for both single level testing and level-dependent testing according to Sections 9.5.5 and 9.5.7 of the ANSI standard respectively is used. Per Section 9.3.5, a 2 mm OD/1 mm ID capillary tube is used to equalize pressure inside the ear canal to ensure proper, continuous, and repeatable fit of the earplugs. Levels from 40 dB to 120 dB in 10 dB steps are included to capture the systems' capabilities at realistic low amplitudes and more extreme high amplitude continuous noise. The below steps highlight the test protocol for both single level (105 dB) testing and level-dependent testing according to the ANSI standard:

Measuring passive insertion loss (PIL) (9.4.3 & 9.5.5):
  Open-ear measurement, LO.;
  Fit the HPD to the ATF (per 9.3.5);
  Waiting period of 120±5 s after final adjustment;
  Closed-ear measurement, LC.;
  Remove the HPD from the ATF; and
  Repeat the above steps for a second measurement;

Measuring total insertion loss (TILSPL) of level-dependent HPDs (9.4.6 & 9.5.7):
  Set test level in room to 75 dB. Open-ear measurement of LO-75;
  Set test level in room to 85 dB. Open-ear measurement of LO-85;
  Set test level in room to 95 dB. Open-ear measurement of LO-95;
  Set test level in room to 105 dB. Open-ear measurement of LO-105;
  Fit the HPD to the ATF (per 9.3.5);
  Waiting period of 120±5 s after final adjustment;
  Set test level in room to 75 dB. Wait 10 s. Closed-ear measurement of LC-75;
  Set test level in room to 85 dB. Wait 10 s. Closed-ear measurement of LC-85;
  Set test level in room to 95 dB. Wait 10 s. Closed-ear measurement of LC-95;
  Set test level in room to 105 dB. Wait 10 s. Closed-ear measurement of LC-105;
  Remove the HPD from the ATF; and
  Repeat the above steps for a second measurement.

The measurement of level-dependent hearing protectors described in the standard is "not to be used for passive HPDs" because "the acoustic nonlinearity on which they are based is not effective at the sound levels used in this continuous noise method." However, by expanding the range of amplitudes (from 75-105 dB to 40-120 dB), the level dependent nature of these devices is captured. Particularly of interest is the insertion loss at low amplitudes to ensure that there is little impact on situational awareness.

Protocol Performance at 40 dB SPL

Figure 23:
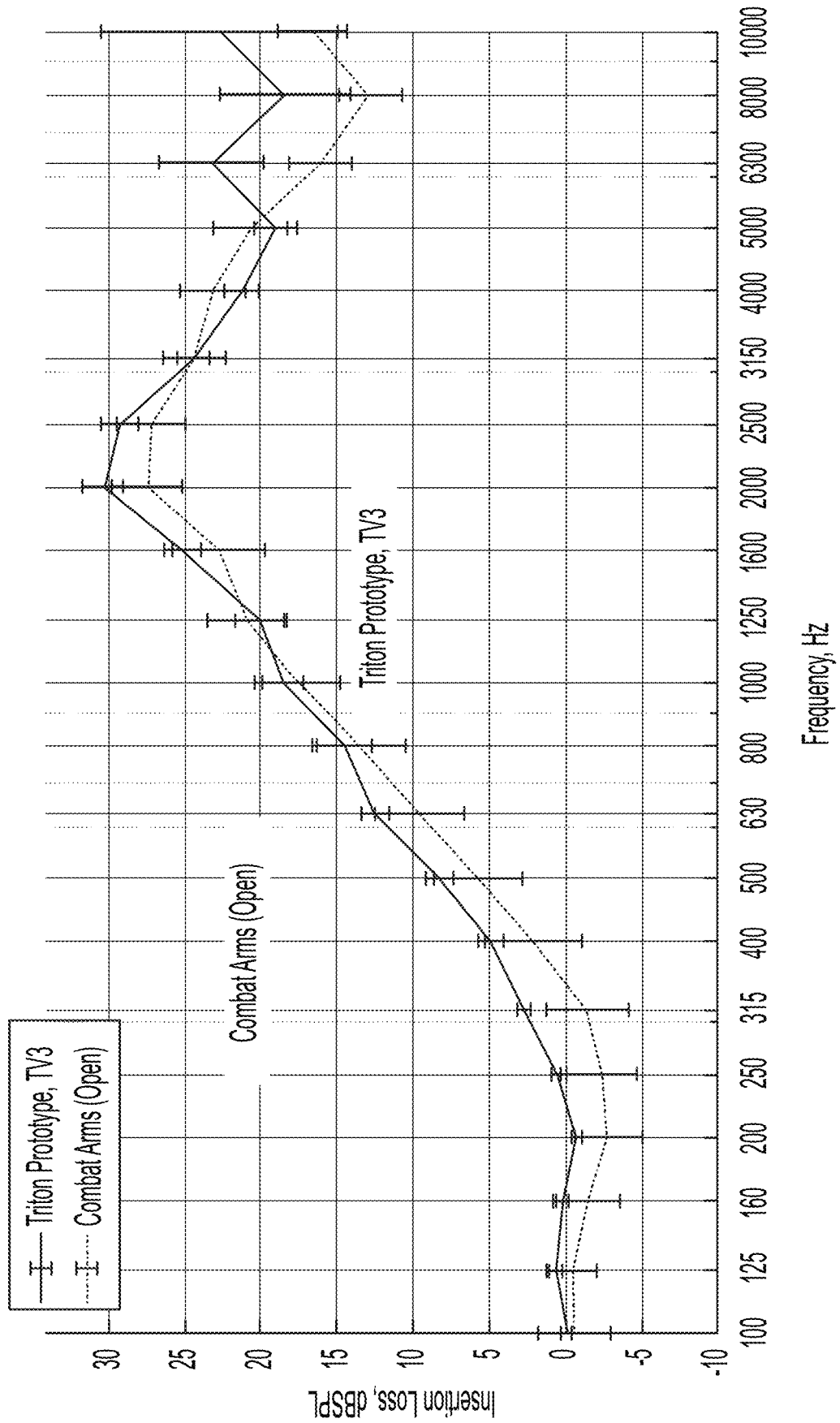
FIG. 23 is a graph showing the average insertion loss at 40 dB of a non-linear acoustic filter in accordance with aspects of the present disclosure.
Figure 24:
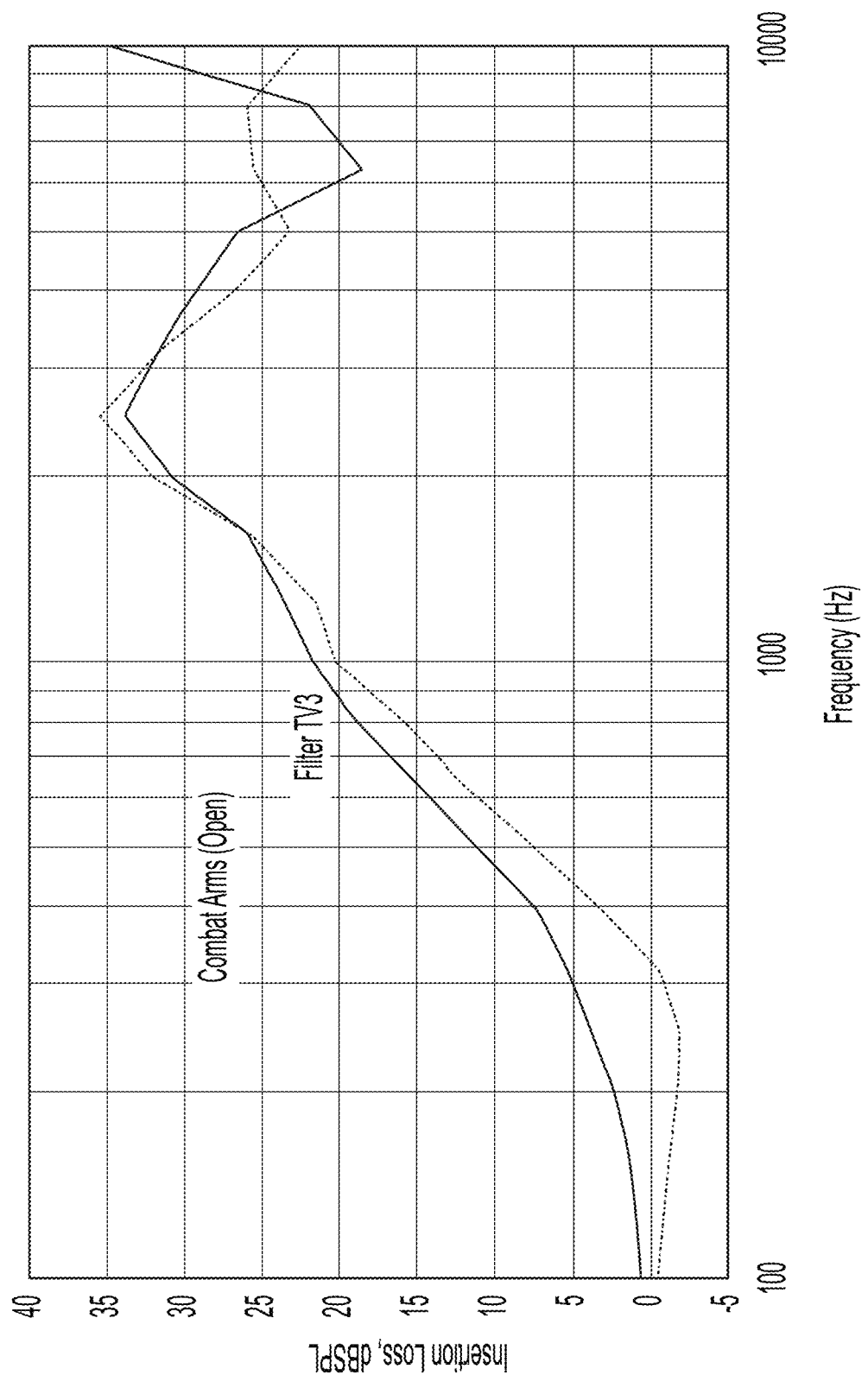
FIG. 24 is a graph showing the average insertion loss at 150 dB of a non-linear acoustic filter in accordance with aspects of the present disclosure.

The test methodology modifies ANSI S12.42-2010 protocols for continuous noise protection by lowering the amplitude from 105 dB (FIG. 24) to 40 dB (FIG. 23). Each package of assembled earplugs is evaluated for 40 dB continuous noise insertion loss using different sizes of earplugs, and each pair is tested twice, for a total of 120 measurements (60 measurements of pairs, but measurements for right and left ear were recorded individually). Based on the results, the size of the earplug does not have a significant impact on the insertion loss. The standard deviation of the measured insertion loss is consistently around 2 dB in each frequency band. Below 400 Hz, the insertion loss is slightly negative. This is likely a result of the resonant chamber formed between the end of the earplug and the measurement microphone and does not indicate a realistic amplification of sound. It does indicate that there is negligible attenuation at lower frequencies.

Example 6

High Amplitude Impulsive Noise Testing

The impulsive peak insertion loss (IPIL) of the non-linear acoustic filter is measured in the laboratory using a shock tube and in the field using real firearms. The test methodology follows ANSI S12.42-2010 protocols for impulsive noise testing at level 148-152 dB and 166-170 dB. Each package of assembled earplugs is evaluated for impulsive peak insertion loss (IPIL) using different sizes of earplugs, and each pair was tested twice, for a total of 120 measurements (60 measurements of pairs, but measurements for right and left ear were recorded individually). Based on the results, the size of the earplug does not have a significant impact on the IPIL. At level 148-152 dB the average IPIL is measured at 17.1 dB with a standard deviation of 2.6 dB. At level 166-170 dB the average IPIL is measured at 24.9 dB with a standard deviation of 2.2 dB.

Figure 12:
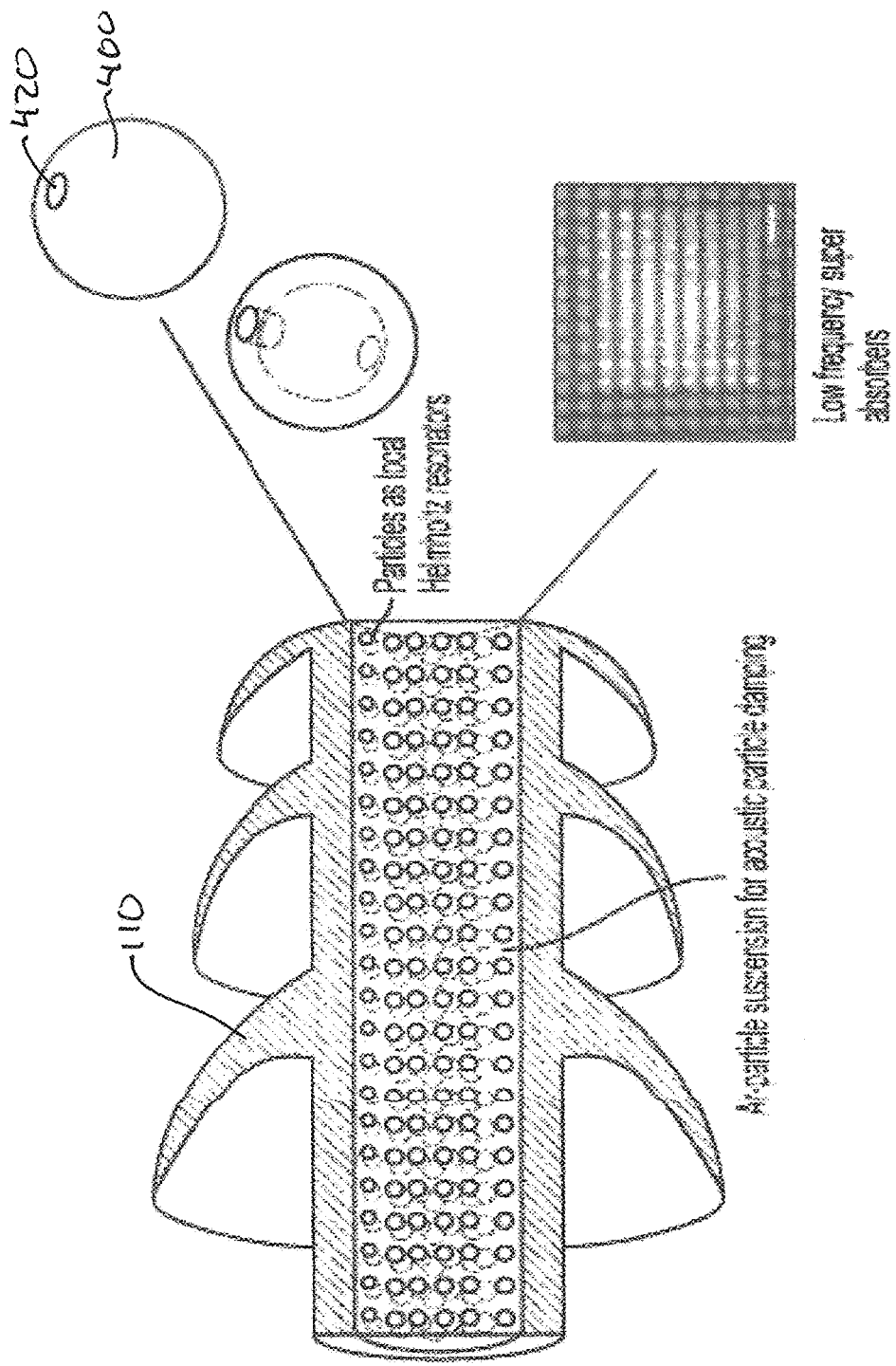
FIG. 12 shows an exemplary of an embodiment that incorporate more than one filter type.

Insertion loss measurements of the non-linear acoustic filter are performed against real firearms at a firing range in Plymouth, MA (FIG. 12). The weapons used in testing are the AR-15 using 5.56 mm NATO rounds and a 9 mm handgun. The test is conducted at an outdoor range to measure the IPIL of the prototypes against relevant firearms. The test methodology follows those used by Fackler et al. (Fackler C, Berger E, Murphy W, Stergar M. *Spectral analysis of hearingprotector impulsive insertion loss*. International Journal of Audiology 2017; 56 (SIP1): 13-21) to measure IPIL as well as Impulse Spectral Insertion Loss (ISIL) with firearms as the acoustic source. The methods used by Fackler et al. are a slight modification to ANSI S12.42-2010. For impulses generated with a firearm, the impulse peak level is controlled by varying the distance from the rifle's muzzle to the location of the ATF and free-field microphone. The GRAS KEMAR 45CB is used as the ATF and the GRAS 67SB is the free-field microphone used to calculate the HRTF:

To capture impulses with a nominal peak of 158 dB, the ATF and free-field microphone was approximately 41 inches to the side of and slightly behind the muzzle of the rifle; and For impulses with a nominal peak level of 145 dB, the ATF and free-field microphone was approximately 82 inches to the side and slightly behind the rifle's muzzle In all cases the rifle's muzzle, the ATF, and the free-field microphones is located approximately 1 m above the ground. The results are summarized in Table 2.

TABLE 2

| | Measured IPIL mean value in dB | |
|---|---|---|
| Impulse Source | AR-15 (158 dB) | 9 mm (153 dB) |
| True Awareness Prototype IPIL | 20.4 | 22.8 |

Example 7

Situation Awareness

Localization testing is performed with the non-linear acoustic filter.

Test Setup

As detailed in Section 7.3.1 of ANSI S3.71-DRAFT, the test setup is arranged as follows:

An array of eight loudspeakers is arranged in four pairs in a circle of radius: 1 m<r<2 m with the measurements made from the center of the head cylinder.

Each pair of loudspeakers shall be 20 degrees apart from the perspective of the position of the listener while the centers of the pairs are separated by 90 degrees.

The loudspeakers should be aligned on the horizontal plane that passes through the ears of the subject.

Each loudspeaker shall be marked with a number (1-8) that is visible and legible to the test subject.

Test Stimuli

As detailed in Section 6 of ANSI S3.71-DRAFT, the test stimulus has the following characteristics:

The noise shall be randomly generated pink noise over the frequency range from 200 Hz to 14 kHz within ±3 dB of the level at 1 kHz when measured at the center of the head cylinder.

Short duration stimuli shall be a total of 250 msec in length with a 10 msec linear or raised cosine ramps at the beginning and end of the stimulus.

Long duration stimuli shall be repetitions of the short duration stimuli with a 50% duty cycle, for a total duration not to exceed 7 seconds.

Stimuli shall be presented at overall levels of 65, 70, and 75 dBA measured at the center of the head cylinder.

Masking Noise

As detailed in Section 8.5.1 of ANSI S3.71-DRAFT, the masking noise has the following characteristics:

Random pink with equal third-octave band levels for center frequencies between 200 Hz and 14 kHz.

Each loudspeaker should output 41 dBA masking noise as measured at the center of the head cylinder, with an overall level of 50 dBA.

Test Procedure

For localization testing, Triton's protocol is laid out in ANSI S3.71-DRAFT Section 8 and summarized below:

Four test blocks shall be used per condition. Each block shall contain either short stimuli or long stimuli presentations, with the ratio of short to long blocks being 3:1.

In each block, the location of the target stimulus will be selected pseudorandomly for each trial, such that each subject will complete 3 trials for each loudspeaker location for each condition in each block of 24 trials.

The short stimuli are presented only once until the subject responds while the long stimulus will play either until the subject responds, or until the 7 s duration expires.

At the beginning of each block of 24 trials, the subject will be asked to align with a location by pointing their nose at one of the labeled markers (A-B; 0°-45° respectively).

After the stimulus is presented and the subject makes their response, the subject should turn back to the alignment marker before proceeding with the next trial.

The subject should complete one block of 24 trials for each of the two alignment points, with the sequence of alignment points chosen randomly without replacement.

Data collection for both alignment points shall be completed with either the open ear condition or the earplug condition before proceeding to the other condition.

In addition to the above procedures, high amplitude stimuli is presented prior to each localization testing condition to simulate an environment with high amplitude sounds in the end stages of testing. This protocol demonstrates the improved detection/localization capability compared to the unoccluded condition following a temporary threshold shift (TTS). The results are summarized in Table 3.

TABLE 3

| | Localization Tests | | | |
|---|---|---|---|---|
| Earplug Name Device | % Correct (Fine) | % Correct (Coarse) | F/B Reversal | Response Time |
| Unoccluded | 78.5% | 98.2% | 0.0% | 1.535 |
| TV3A | 81.8% | 97.8% | 0.0% | 1.644 |

Based on these results, the non-linear acoustic filter design, fitting deep in the ear canal and having minimal impact on the HRTF, offers near-unoccluded localization capability.

Example 8

Detection Recognition/Identification, Localization, and Communications Testings

To quantify the auditory situational awareness (ASA) effects of the non-linear acoustic filter, the method developed by Casali based on Detection Recognition/Identification, Localization, and COMmunications testing methodology (DRILCOM) is used (Casali, J. (2012). In-Field Human Factors Evaluation of the Effects of Augmented Hearing Protection/Enhancement Devices (HPEDs) on Auditory Detection and Identification with Relevance to Situation Awareness for the U.S. Marines. 2012 *Noise Induced Hearing Loss Review* (pp. 6-10). The testing demonstrates that:

Detection: the non-linear acoustic filter provides superior detection ability to Combat Arms in nearly all cases. The non-linear acoustic filters are notably better than the Combat Arms when the signal is directly to the right (3 o'clock) and to the left (9 o'clock) of the subject.

Recognition/Identification: the non-linear acoustic filter do not impact the subjects' ability to identify sounds compared to the open ear. The ability to recognize and identify the test signals is virtually the same across the SNRs for both hearing protection devices as well as open ear.

Localization: at the "low" test condition (signal is 53 dBA) subjects unsurprisingly performed best without hearing prediction. Interestingly, at the "high" test condition (signal is 85 dBA) subjects performed best with the non-linear acoustic filter.

Communication: the results show that the SNR loss from the non-linear acoustic filter is less than 1 dB different from the open ear and this difference is imperceptible to a human observer. There is no substantial difference across the hearing protection devices and the open ear.

Example 8: Another Embodiment with a Tesla Valve Non-Linear Acoustic Filter (TV5)

Figure 25:
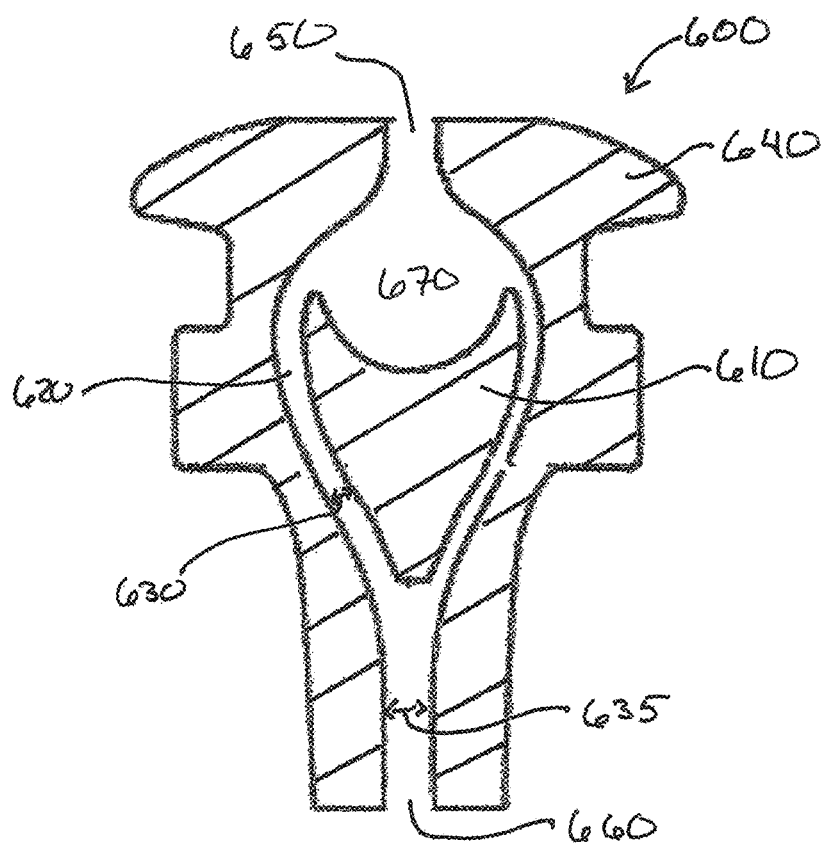
FIG. 25: shows an exemplary non-linear acoustic filter using Tesla Valve.

An earplug similar (FIG. 25) to that described in Example 1 was prepared and tested. A Silicone triple-flanged eartip were used as housing. The exterior shape of the filter matched the interior shape of the triple-flanges eartip to ensure a secure fit. A non-linear acoustic filter 600 in the form of a Tesla valve is inserted into the bore of the housing. The non-linear acoustic filter is printed using stereolithography method. The material used in the process simulates the properties and aesthetics of polypropylene and has characteristics necessary for this part. The non-linear acoustic filter employed here has an orifice diameter (i.e., aperture at both the source side 650 and ear-side of the filter 660) of 0.76 mm. The non-linear acoustic filter has a channel offset 630

Figure 26:
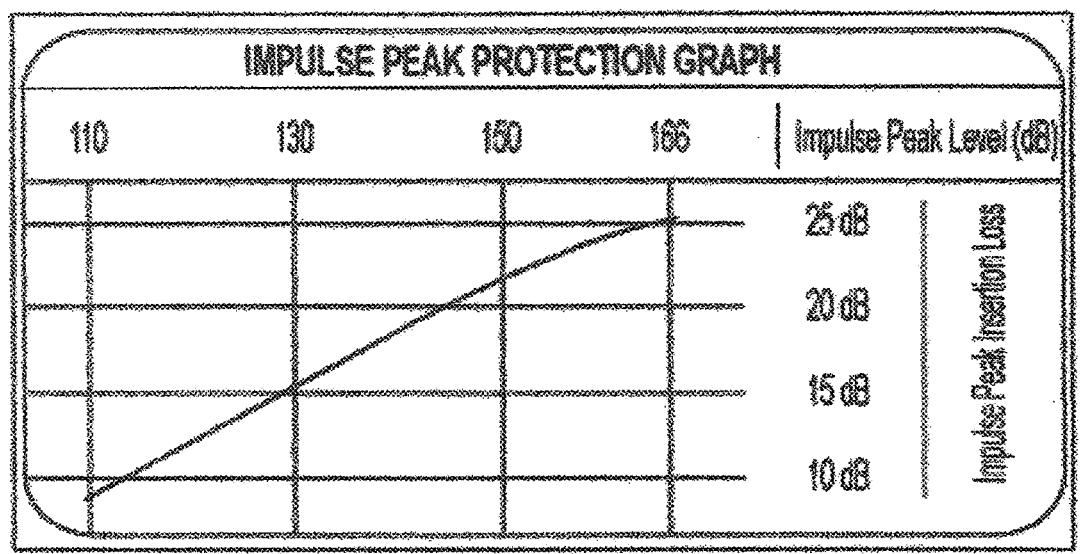
FIG. 26: impulse peak insertion loss as a function of impulse peak noise level.

(i.e., distance between the filter "bulb" and the surrounding material) of 0.4 mm). The overall filter length is 10 mm. FIG. 26 shows the IPIL of the TV5 device. The plot shows the noise attenuation (Impulse Peak Insertion Loss, vertical axis on the plot) at different impulse Peak levels (horizontal axis on the plot). The higher the insertion loss the better.

L1 level in FIG. 16 is at 150 dB. The insertion loss for different designs (TV0, TV1, TV2, TV3, TV4) are between 12.5 to 18.3 dB. The product certified result shows an insertion loss of 22 dB at 150 dB peak noise level. Significantly better.

L2 level in FIG. 16 is at 158 dB. The insertion loss for different designs (TV0, TV1, TV2, TV3, TV4) are between 19 to 27.5 dB. The product certified result shows an insertion loss of 25 dB at 158 dB peak noise level. Better than all designs shown on FIG. 16 except for TV3.

What is claimed is:

1. An earplug, for use by a user having an ear including an ear canal having an external orifice at one end and an eardrum at the other, the earplug comprising:

a housing extending generally linearly along a longitudinal axis of the earplug and defining a bore; and a non-linear acoustic filter extending generally linearly along the longitudinal axis of the earplug and disposed at least partially in the bore, the non-linear acoustic filter having a proximal end adjacent to the eardrum of the user, a distal end adjacent to the external orifice of the ear canal, and a middle section between the proximal end and the distal end, wherein the non-linear acoustic filter comprises one or more sets of individual microspheres;

wherein the microspheres are surrounded by a mesh to keep them together;

wherein the earplug is designed to occupy the inner part of an ear canal.

2. The earplug of claim 1, wherein the microspheres each have a diameter of about 345 µm to 435 µm.

* * * * *